United States Patent [19]

Marcinowski et al.

[11] Patent Number: 4,767,707
[45] Date of Patent: Aug. 30, 1988

[54] IMMOBILIZATION OF ENZYMES WITH A WATER-SOLUBLE GLYCIDYL ETHER

[75] Inventors: Stefan Marcinowski, Ludwigshafen; Axel Sanner, Frankenthal; Chung-Ji Tschang, Bad Durkheim; Wolfgang Ladner, Ludwigshafen; Norbert Greif, Bobenheim, all of Fed. Rep. of Germany

[73] Assignee: BASF Aktiengesellschaft, Ludwigshafen, Fed. Rep. of Germany

[21] Appl. No.: 889,392

[22] Filed: Jul. 25, 1986

[30] Foreign Application Priority Data

Jul. 27, 1985 [DE] Fed. Rep. of Germany ....... 3527014

[51] Int. Cl.⁴ .................... C12N 11/04; C12N 11/08
[52] U.S. Cl. ...................................... 435/182; 435/180
[58] Field of Search ............... 435/174, 177, 180, 181, 435/182

[56] References Cited

U.S. PATENT DOCUMENTS 4,334,027  6/1982  Klein et al. ........................ 435/178

FOREIGN PATENT DOCUMENTS 2835874  6/1983  Fed. Rep. of Germany .

OTHER PUBLICATIONS

Mosbach et al., Acta Chem. Scan., 20, 2807 (1966).

*Primary Examiner*—David M. Naff
*Attorney, Agent, or Firm*—Keil & Weinkauf

[57] ABSTRACT

Enzymes are immobilized by mixing the following components with one another in aqueous solution:
(a) an enzyme or a dispersed microorganism,
(b) a water-soluble glycidyl ether, prepared by subjecting from 1 to 30 equivalents of an epoxide of the formula I

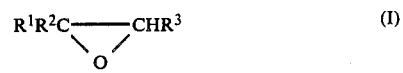

where $R^1$, $R^2$ and $R^3$ are each hydrogen, methyl or ethyl, to an addition reaction with 1 equivalent (based on OH groups) of a polyfunctional alcohol of 2 to 6 carbon atoms or of a mono- or disaccharide to produce an adduct, reacting the adduct with epichlorohydrin and, if required, then carrying out cyclization to give the epoxide, and
(c) a water-soluble amine possessing two or more NH groups, if necessary in a partially neutralized form, and allowing the mixture thus obtained to gel.

6 Claims, No Drawings

IMMOBILIZATION OF ENZYMES WITH A WATER-SOLUBLE GLYCIDYL ETHER

The present invention relates to a novel process for the immobilization of enzymes.

Immobilized enzymes and their use are known (cf. Methods in Enzymology, Vol. 44: Immobilized Enzymes, Academic Press 1976, and Immobilized Enzymes, Halsted Press 1978).

In order to immobilize enzymes in a very simple manner and without great expense, attempts have been made to embed the enzymes in gels. An example of this is the preparation of an enzyme-containing aqueous gel using acrylamide and methylene-N,N'-bisacrylamide (Acta Chem. Scan. 20 (1966), 2807). In such a gel, however, the immobilized enzyme is only mechanically enclosed without being covalently bonded. Consequently, when the gel is used, a substantial amount of the enzyme is extracted. In order to avoid this, the enzyme can be reacted with vinyl-containing monomers which are capable of reacting with, for example, amino or hydroxyl groups of the enzyme (Methods in Enzymology, loc. cit.). After such a treatment, the enzyme behaves like a vinyl-containing monomer and is covalently bonded in the resulting gel during polymerization. However, disadvantages of this process are that an additional step is required for the preparation of the insoluble enzyme preparation and the monomers which are suitable are generally difficult to obtain and have an adverse effect on the enzymatic activity. A process which attempts to avoid all possible disadvantages as completely as possible is described in German Laid-Open Application DOS No. 2,835,874. In this process, an enzymatically active biomass is mixed first with a polyfunctional epoxide prepolymer and then with a polyfunctional amine, and the mixture is finally converted to a macroporous, bead-like preparation via a plurality of stages, with the aid of a polyelectrolyte. However, this process is very complicated and requires extremely expensive apparatus to implement it on an industrial scale.

It is an object of the present invention to provide a very simple immobilization process which avoids the disadvantages of the above methods.

We have found that this object is achieved by a process for the immobilization of enzymes or microorganisms, wherein the following components are mixed with one another in aqueous solution:
(a) an enzyme or a dispersed microorganism,
(b) a water-soluble glycidyl ether, prepared by subjecting from 1 to 30 equivalents of an epoxide of the formula

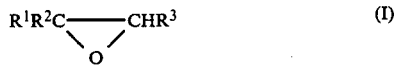  (I)

where $R^1$, $R^2$ and $R^3$ are each hydrogen, methyl, or ethyl, to an addition reaction with 1 equivalent (based on OH groups) of a polyfunctional alcohol of 2 to 6 carbon atoms or of a mono- or disaccharide, reacting the resulting adduct with epichlorohydrin and, if required, then carrying out cyclization to give the epoxide, and
(c) a water-soluble amine possessing two or more NH groups, if necessary in a partially neutralized form, and the mixture thus obtained is allowed to gel.

The enzymes used for immobilization need not be pure. It is also possible to use solutions which contain cell fragments. However, only enzymes which are stable under the pH conditions prevailing during gelling (pH 7.5-11) are suitable. Useful enzymes or enzyme-containing products are glucose isomerase, alkaline phosphatase, alcohol dehydrogenase, elastase, D-hydantoinase, leucine aminopeptidase, phosphodiesterase, proteases, asparaginase, esterase, beta-galactose dehydrogenase, glycerokinase, lipases, D-aminoacid oxidase, arginase, nuclease and uricase.

The water-soluble glycidyl ether obtained from the epoxide and the polyfunctional alcohol or the mono- or disaccharide and epichlorohydrin is of the formula II

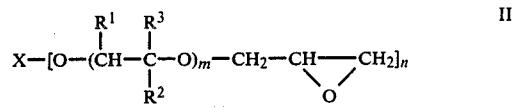  II where m is from 1 to 30, n is an integer from 2 to 10, X is the radical of the polyfunctional alcohol or of the mono- or disaccharide and $R^1$, $R^2$ and $R^3$ have the above meanings. As a rule, n corresponds to the number of OH groups in the polyfunctional alcohol or in the mono- or disaccharide.

$R^1$, $R^2$ and $R^3$ are each preferably hydrogen. In formula II, the substituents $R^1$, $R^2$ and $R^3$ need not be identical over all —$R^1$CH—$CR^2R^3$—O units. Compounds possessing different chain members are obtained, for example, by condensation of different epoxides.

Half, preferably two thirds, of the total number of radicals $R^1$, $R^2$ and $R^3$ should be hydrogen, so that the products are water-soluble. Preferred epoxides are propylene oxide, butylene oxide and in particular ethylene oxide.

Instead of the compounds II, it is also possible to use the corresponding chlorohydrins, which are converted to the epoxide intermediate by the action of the amine.

Examples of suitable polyfunctional alcohols are glycerol, pentaerythritol, trimethylolpropane and sorbitol. Glucose is a particularly suitable monosaccharide, and sucrose a particularly suitable disaccharide.

Useful water-soluble amines are ammonia, primary aliphatic amines, such as methylamine, ethylamine, propylamine or butylamine, primary or secondary aliphatic diamines, e.g. $H_2N—(CH_2)_n—NH_2$, where n is 2 to 6, and aliphatic polyimines. Polyethyleneimine is the preferred amine. The amount of amine is chosen so that the ratio of epoxide groups to amino groups is from 1:1.4 to 1:20, preferably from 1:1.7 to 1:6. In order to prevent the enzyme to be immobilized from being damaged by excessively alkaline conditions, it is advisable partially to neutralize the amine with an acid prior to mixing. Monobasic mineral acids, such as hydrochloric acid or nitric acid, are particularly useful for this purpose. The preferred pH is from 8 to 9.

The ratio of epoxide and amine to the amount of enzymatically active solution or suspension should be chosen so that, on the one hand, the solubility of the two reactive components is ensured and, on the other hand, the gel produced is not too soft as a result of excessive dilution of the system. The correct ratio of the two components can most advantageously be determined by a preliminary experiment.

Regarding the order in which mixing is carried out, it is preferable if the epoxide is added first and then the amine. The temperature during mixing can be from 0° C. to the temperature at which substantial denaturing of the enzyme being immobilized is just avoided. Mixing is preferably carried out at room temperature. The same rules apply regarding the temperature during gel formation.

Enzymes or enzyme-containing material (cells and cell constituents) can be incorporated into the gel up to concentrations such that either the mechanical strength of the gel suffers as a result or the activity of the enzyme can no longer be fully utilized owing to restriction of diffusion. In the case of a pure enzyme, the upper limit is about 30–50 mg/g of gel.

The resilience and density of the enzymatically active gels can be varied if finely divided inert materials, e.g. active carbon, kieselguhr, materials such as those used for reinforcing plastics, or plastic powders are added to the gel-forming mixture in an amount of up to 100% by weight, based on the said mixture. It is advisable to determine the compatibility of the inert material with the enzyme by means of a small test batch.

Another method of obtaining an enzymatically active preparation having particularly high strength is to incorporate the gel-forming mixture into the pores of an inert, porous material, e.g. kieselguhr, a glass fiber mat, a porous ion exchanger, an open-cell foam, a synthetic absorbent or a porous mineral, such as clay or pumice. Conversely, it is also possible, for example in order to vary the density or the compressibility, to incorporate inert substances, such as those stated above, sand or another finely divided material, into the gel. Finally, the enzymatically active gel may also be additionally strengthened by being dried before use.

The gel can also be used in anhydrous or very substantially anhydrous solvents if this is appropriate for the reaction to be carried out and the immobilized enzyme is active under these conditions.

In the immobilization of enzymes which require metal ions in order to display their activity, it is advisable to add a sparingly soluble oxide or salt of the appropriate metal, as far as possible in a finely powdered form, to the gel-forming mixture.

In order to avoid a loss of activity due to diffusion, the gel formed by the present immobilization process can be prepared in the form of a film or can be comminuted. To do this, it is forced through a sieve or passed through an extruder. In order to meet the technical requirements in practice, a particle size of about 0.1–5 mm is desirable. Another method of obtaining a finely divided gel is to suspend the gel-forming mixture in a water-immiscible organic solvent. The suspension is stirred until gel formation is complete. Finally, the gel is obtained in the form of small beads having a diameter of about 0.2–2 mm, and can be separated off from the solvent with the aid of a sieve.

The present immobilization process is particularly simple since it comprises only the mixing, hardening and comminution steps. The use of water-soluble epoxides permits thorough mixing of epoxide and enzyme, facilitating covalent bonding of the enzyme to the resulting gel via the epoxide groups. The extraordinary increase in the life of D-hydantoinase after immobilization by the present process is particularly surprising.

The Examples which follow illustrate the invention.

EXAMPLE 1

Preparation of glycidyl ethers (a)

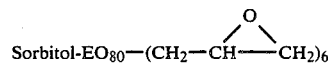

14.8 g of $BF_3$ dihydrate are added to 3,705 g of sorbitol-$EO_{80}$ (reaction product of 1 mole of sorbitol with 80 moles of ethylene oxide; cf. Houben-Weyl, Methoden der Org. Chemie 14/2 (1963), 450), after which 555 g of epichlorohydrin are added dropwise to the stirred mixture at 70° C. Stirring is continued for a further 2 hours at this temperature, after which 528 g of 50% strength sodium hydroxide solution are added dropwise at from 20 to 35° C. in the course of from 1 to 2 hours. Stirring is continued until about 90% of the sodium hydroxide solution has been consumed, consumption of this solution being monitored titrimetrically. The major part of the water is distilled off at 70° C. under reduced pressure from a water pump, and the remainder is sucked off at elevated temperatures (70° C.). This procedure gives 3,439 g (85%) of a reaction product of epichlorohydrin with sorbitol-$EO_{80}$, which has an epoxide titer of from 1.2 to 1.3 meq/g. The product is of the formula II, where X is the sorbitol radical, $R^1$, $R^2$ and $R^3$ are each hydrogen, m is 1.34 and n is 6.

The following are prepared by a method similar to that described under (a):

(b) Reaction product of epichlorohydrin with pentaerythritol-$EO_{40}$; yield 86%; epoxide titer 1.6 meq/g. The product is of the formula II, where X is the pentaerythritol radical, $R^1$, $R^2$ and $R^3$ are each hydrogen, m is 10 and n is 4.

(c) As for (b), but using pentaerythritol-$EO_{57}$; yield 83%; epoxide titer 0.9 meq/g; m=14.3 and n=4.

(d) Reaction product of epichlorohydrin with glycerol-$EO_{60}$; yield 78%; epoxide titer 0.9 meq/g. The product is of the formula II, where X is the glycerol radical, $R^1$, $R^2$ and $R^3$ are each hydrogen, m is 20 and n is 3.

(e) Reaction product of epichlorohydrin with sorbitol-$EO_{30}$; yield 84%; epoxide titer 1.9 meq/g. The product is of the formula II, where X is the sorbitol radical, $R^1$, $R^2$ and $R^3$ are each hydrogen, m is 5 and n is 6.

(f) Reaction product of epichlorohydrin with trimethylolpropane-$EO_{40}$; yield 81%; epoxide titer 1.2 meq/g. The product is of the formula II, where X is the trimethylolpropane radical, $R^1$, $R^2$ and $R^3$ are each hydrogen, m is 13.4 and n is 3.

EXAMPLE 2

Immobilization of lipase

Gels are prepared by mixing the components in the order stated below, in a beaker at room temperature, and leaving the mixture to stand overnight. The gels are comminuted by forcing them through a sieve having a mesh size of 2 mm.

(a) 10 g of a solution of 2.3 g of pancreas lipase (Fluka No. 62,000) in 7.7 g of 0.05M tris(tris-hydroxymethylamine hydrochloride) buffer at pH 8.5 6.5 g of a glycidyl ether, prepared as described in Example 1a) 4 g of polyethyleneimine solution brought to pH 9.0 with hydrochloric acid; molecular weight of the polyethyleneimine: about 40,000; polyethyleneimine content: 25% by weight.

(b) 5 g of a solution of pancreas lipase (see a) 5 ml of 0.05M tris buffer solution, pH 8.5 6.5 g of glycidyl ether according to Example 1a 4 g of polyethyleneimine solution (see a).

The lipase activity is determined at 30° C. in a pH-stat. 1 g of tributyrin (glycerol tributyrate) is emulsified in 50 ml of 0.02M borax/HCl buffer solution at pH 7.5. For comparison, 25 mg of non-immobilized pancreas lipase are employed, with vigorous stirring. 0.5N of sodium hydroxide solution is metered in to keep the pH constant. 3.3 $\mu$mol of NaOH per mg of lipase per minute are consumed.

When this experiment is repeated with equivalent amounts of immobilized lipase, the following values are obtained:
Gel (a) 0.29 $\mu$mol of NaOH/mg of lipase per minute
Gel (b) 0.26 $\mu$mol of NaOH per mg of lipase per minute This demonstrates that the lipase, which is generally difficult to immobilize, is immobilized by this process.

EXAMPLE 3

Immobilization of subtilisin 14 ml of 0.02M borax buffer solution (pH 7.5) which is also 0.002M in zinc sulfate and contains 60 mg of subtilisin (protease type VIII from Sigma) are mixed with 9.75 g of a glycidyl ether according to Example (1b) and with 6 g of polyethyleneimine/HCl solution (molecular weight of the polyethyleneimine about 40,000, pH 8.5, polyethyleneimine content 25% by weight) in a beaker at room temperature. The mixture hardens overnight and is comminuted by forcing it through a sieve having a mesh size of 0.8 mm.

The enzymatic activity is determined by cleaving

H—D-valyl—L-leucyl—L-lysine—p-nitroanilide dihydrochloride

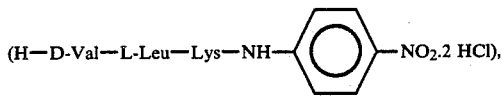

the amount of p-nitroaniline liberated ($\epsilon$=9.62 l.mmole$^{-1}$.cm$^{-1}$) being determined by measuring the light absorption at 405 nm. Solutions employed:
buffer: borax, 0.02M, pH 7.5.
substrate:

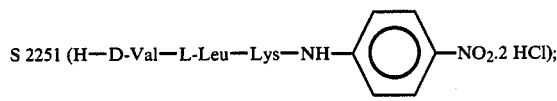

Kasi Diagnostica, Stockholm, Sweden). The substrate is employed in a borax buffer solution (see above) in a concentration of 5 mg/ml.
enzyme: Protease type VIII from Sigma. For comparative measurements, the enzyme is employed in a borax buffer solution (see above) in a concentration of 1.5 mg/ml.

The activity is determined by the following procedure: 1 ml of substrate solution, 1.6 ml of buffer solution and 400 $\mu$l of enzyme solution or one equivalent of immobilized enzyme are introduced, at 23° C., into a cell having a bath length of 1 cm, this cell is shaken slowly and continuously by hand for 10 minutes and the extinction is then measured. Where the immobilized enzyme is used, the latter has to be caused to settle out beforehand by centrifuging for a short time (10 s). The free enzyme is found to have an activity of 0.024 $\mu$mol of p-nitroaniline per mg of enzyme per minute. The corresponding value for the immobilized enzyme is 0.019 $\mu$mol of p-nitroaniline per mg of enzyme per minute.

EXAMPLE 4

Immobilization of D-hydantoinase

A 10% strength by weight aqueous suspension of the lyophilized, D-hydantoinase-active microorganism CBS 303.80 disrupted by means of ultrasound (German Laid-Open Application DOS No. 3,031,151) is employed. The immobilized enzyme is prepared by mixing the components listed below in a beaker at room temperature in the order stated, hardening overnight and comminuting the resulting gel by forcing it through a sieve of 1 mm mesh size.
Starting materials:
Experiment (4a)
    2.5 ml of a suspension of the microorganism CBS 303.80 (see above)
    1 g of a glycidyl ether according to Example 1e)
    0.9 ml of 100% pure methylamine
Experiment (4b)
    2.5 ml of a suspension of the microorganism CBS 303.80 (see above)
    1 g of the glycidyl ether according to Example 1e)
    1.2 ml of 3-(2-aminoethyl)-aminopropylamine
Experiment (4c)
    2.5 ml of a suspension of the microorganism CBS 303.80 (see above)
    1 g of the glycidyl ether according to Example 1c)
    0.05 g of finely powdered manganese dioxide
    1 g of polyethylene solution brought to pH 9 with hydrochloric acid. The molecular weight of the polyethyleneimine is about 40,000 and the polyethyleneimine content 25% by weight.

The enzymatic activity is determined at 60° C. in a pH-stat. 5-Methylthioethylhydantoin in a concentration of 10 mg/ml in 0.1M tris/HCl buffer solution (pH 8.5) is used as the substrate. The activity is determined from the consumption of 1N sodium hydroxide solution. In a comparative test, the free microorganism CBS 303.80 disrupted by means of ultrasound is found to possess an activity which leads to the consumption of 402 $\mu$mol of NaOH per g of dry microorganism per minute. The following values are obtained for the immobilized enzymes:
Experiment (4a)
    1 $\mu$mol of NaOH per g of immobilized enzyme per minute.
Experiment (4b): 2 $\mu$mol of NaOH per g of immobilized enzyme per minute.
Experiment (4c):
    11 $\mu$mol of NaOH per g of immobilized enzyme per minute.

After being used for 1 week, the immobilized enzymes still possess more than 50% of their initial activity, whereas the free microorganism loses its activity after about 4 hours.

We claim:

1. A process for immobilizing an enzyme or microorganism consisting essentially of mixing the following components with one another in aqueous solution:
   (a) an enzyme or a dispersed microorganism,
   (b) a water-soluble glycidyl ether, prepared by subjecting from 1 to 30 equivalents of an epoxide of the formula I $$R^1R^2C\underset{O}{\overset{}{\diagdown\diagup}}CHR^3 \qquad (I)$$

where $R^1$, $R^2$ and $R^3$ are hydrogen, methyl or ethyl, to an addition reaction with 1 equivalent, based on OH groups, of a polyfunctional alcohol of 2 to 6 carbon atoms or of a mono- or disaccharide to produce an adduct, reacting the adduct with epichlorohydrin to give the glycidyl ether, and
   (c) a water-soluble amine possessing to or more NH groups
   and allowing the mixture thus obtained to gel.

2. The process of claim 1 wherein the enzyme is lipase, alkaline protease or D-hydantoinase.

3. The process of claim 1 wherein the water-soluble amine is in partially neutralized form.

4. The process of claim 1 wherein following reaction with epichlorohydrin, cyclization is carried out to give the glycidyl ether.

5. A process for immobilizing an enzyme or microorganism consisting essentially of mixing the following components with one another in aqueous solution:
   (a) an enzymne or a dispersed microorganism,
   (b) a water-soluble glycidyl ether, prepared by subjecting from 1 to 30 equivalents of an epoxide of the formula I $$R^1R^2C\underset{O}{\overset{}{\diagdown\diagup}}CHR^3 \qquad (I)$$

where $R^1$, $R^2$ and $R^3$ are each hydrogen, methyl or ethyl, to an addition reaction with 1 equivalent, based on OH groups, of a polyfunctional alcohol of 2 to 6 carbon atoms or of a mono- or disaccharide to produce an adduct, reacting the adduct with epichlorohydrin and then carrying out cyclization to give the glycidyl ether, and
   (c) a water-soluble amine possessing two or more NH groups in a partially neutralized form
   and allowing the mixture thus obtained to gel.

6. The process of claim 5 wherein the enzyme is lipase, alkaline protease or D-hydantoinase.

* * * * *